United States Patent
Bychkov et al.

(10) Patent No.: US 10,293,124 B2
(45) Date of Patent: May 21, 2019

(54) RESPIRATION SYSTEM AND RESPIRATION APPARATUS AND METHOD

(71) Applicant: WEINMANN GERAETE FUER MEDIZIN GMBH & CO. KG, Hamburg (DE)

(72) Inventors: Igor Bychkov, Karlsruhe (DE); Florian Stockwald, Karlsruhe (DE)

(73) Assignee: Loewenstein Medical Technology S.A., Luxembourg (LU)

(*) Notice: Subject to any disclaimer, the term of this patent is extended or adjusted under 35 U.S.C. 154(b) by 796 days.

(21) Appl. No.: 14/834,637

(22) Filed: Aug. 25, 2015

(65) Prior Publication Data
US 2016/0058962 A1    Mar. 3, 2016

(30) Foreign Application Priority Data
Aug. 28, 2014    (DE) .................. 10 2014 012 793

(51) Int. Cl.
*A61M 16/00*    (2006.01)
*G16H 40/40*    (2018.01)

(52) U.S. Cl.
CPC .......... *A61M 16/00* (2013.01); *A61M 16/024* (2017.08); *G16H 40/40* (2018.01); *A61M 2205/50* (2013.01); *A61M 2205/58* (2013.01)

(58) Field of Classification Search
CPC ....... G16H 40/40; G16H 40/60; A61M 16/00; A61M 16/024; A61M 2205/50
See application file for complete search history.

(56) References Cited

U.S. PATENT DOCUMENTS

| | | | | |
|---|---|---|---|---|
| 8,316,350 | B2* | 11/2012 | Bendig | G06F 9/44536 717/116 |
| 8,726,266 | B2* | 5/2014 | Kiaie | G06F 8/65 600/365 |
| 9,721,063 | B2* | 8/2017 | Hayter | G06F 19/32 |
| 2006/0130073 | A1 | 6/2006 | Faist et al. | |
| 2008/0097168 | A1* | 4/2008 | Hopermann | A61B 90/36 600/300 |

(Continued)

FOREIGN PATENT DOCUMENTS

| | | |
|---|---|---|
| EP | 1659489 A1 | 5/2006 |
| WO | 2009023296 A1 | 2/2009 |
| WO | 2010141922 A1 | 12/2010 |

*Primary Examiner* — Joshua Lee
(74) *Attorney, Agent, or Firm* — Abel Schillinger, LLP

(57) ABSTRACT

The present invention relates to methods for operating a respiration apparatus and a respiration system, and also a respiration apparatus and a respiration system. The respiration system comprises a respiration apparatus and a computer software program for an external computer to operate the respiration apparatus. The respiration apparatus comprises a processor device and an apparatus software program and an apparatus configuration. The validities of the computer software, the apparatus software and the apparatus configuration are in each case characterized by a version. The versions are compared with one another to detect a version conflict. If invalid versions are present, the computer software is provided with a program component with a limit value and a plausibility rule, or the setting parameters are sorted into a first group and a second group. The setting parameters of the first group are retained.

18 Claims, 1 Drawing Sheet

(56) References Cited

U.S. PATENT DOCUMENTS

| | | | | |
|---|---|---|---|---|
| 2008/0127165 | A1 | 5/2008 | Mullis et al. | |
| 2009/0113413 | A1* | 4/2009 | Reinz | G16H 40/40 |
| | | | | 717/173 |
| 2010/0313105 | A1* | 12/2010 | Nekoomaram | G06F 8/654 |
| | | | | 714/807 |
| 2012/0036503 | A1* | 2/2012 | Reeves | G09B 9/02 |
| | | | | 717/168 |
| 2014/0089531 | A1* | 3/2014 | Bhogal | G06F 9/4411 |
| | | | | 710/8 |
| 2014/0163919 | A1* | 6/2014 | Manigel | A61M 5/172 |
| | | | | 702/123 |
| 2015/0169319 | A1* | 6/2015 | Ahmed | G06F 8/71 |
| | | | | 717/122 |
| 2015/0199192 | A1* | 7/2015 | Borges | G06F 8/65 |
| | | | | 717/172 |
| 2015/0370983 | A1* | 12/2015 | Vial | G06F 19/3406 |
| | | | | 705/2 |
| 2016/0367779 | A1* | 12/2016 | Landis | A61M 16/049 |

\* cited by examiner

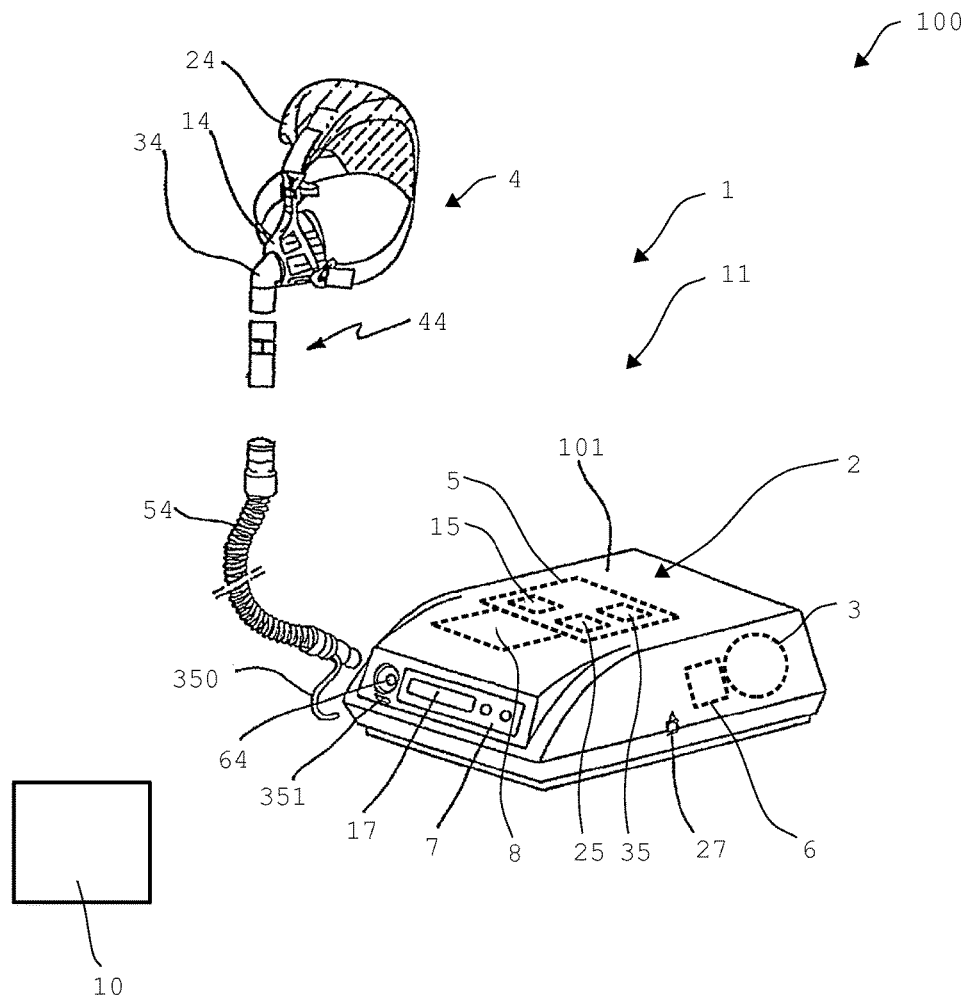

RESPIRATION SYSTEM AND RESPIRATION APPARATUS AND METHOD

CROSS-REFERENCE TO RELATED APPLICATIONS

The present application claims priority under 35 U.S.C. § 119 of German Patent Application No. 10 2014 012 793.1, filed Aug. 28, 2014, the entire disclosure of which is expressly incorporated by reference herein.

BACKGROUND OF THE INVENTION

Field of the Invention

The present invention relates to a respiration apparatus and a method for operating a respiration apparatus and a respiration system and a method for operating a respiration system with at least one respiration apparatus. The respiration apparatus comprises at least one processor device and at least one apparatus software program. The respiration system comprises at least one respiration apparatus and at least one computer software program for an external computer to operate the respiration apparatus. The validities of the computer software, the apparatus software and the apparatus configuration are characterized in each case by at least one version. The versions are at least partially compared with one another in order to detect a version conflict.

Discussion of Background Information

Modern respiration apparatuses are normally operated with correspondingly adapted software solutions. As a result, for example, individually settable respiration modes or an automatic detection of respiratory disorders can be particularly effectively implemented. A software program for the respiration apparatus itself and a software program for an external computer from which the apparatus can be read and controlled are often provided. Moreover, a configuration file which, for example, specifies the reference values or limit values for the respiration parameters to be set for the respiration is often stored in the apparatuses.

A regular updating of the software is helpful or necessary in order to guarantee fault-free operation. However, incompatible versions of the individual software elements may be present as a result of updates of this type.

Specific functions, such as e.g. the setting or reading of the respiration apparatus via PC software, may no longer operate correctly as a result of incompatible versions of this type. Moreover, previous configurations or respiration settings may no longer be available and may have to be recreated as a result of the updating of software on the respiration apparatus or the computer, which in most cases is very costly. In very unfavorable cases, incompatible versions may even adversely affect the provision of the respiration.

In view of the foregoing, it would be advantageous to have available a respiration apparatus and a respiration system and a method for operating a respiration apparatus and a respiration system with which a reliable operation can be guaranteed independently of software updates.

SUMMARY OF THE INVENTION

The present invention provides methods, a respiration apparatus and a respiration system as set forth in the independent claims. Some advantageous but optional features of the present invention are set forth in the dependent claims. Further advantages and features are indicated in the general description and the description of the example embodiment.

The method according to the invention serves to operate at least one respiration apparatus. The respiration apparatus comprises at least one processor device to control a plurality of apparatus functions with at least one apparatus software program and with at least one apparatus configuration with setting parameters. A validity of the apparatus software and a validity of the apparatus configuration are characterized in each case by at least one version. The versions are compared with one another in order to detect at least one version conflict between the apparatus software and the apparatus configuration. The setting parameters of the apparatus configuration are read if an invalid version of the apparatus configuration and a valid version of the apparatus software are present. The setting parameters of the apparatus configuration are sorted into at least a first group and at least a second group. The first group comprises setting parameters that are unaffected by the version conflict. The second group comprises setting parameters that are affected by the version conflict. The setting parameters of the first group are retained.

The method according to the invention for operating the respiration apparatus has many advantages. One significant advantage is that, if at least one invalid version is present, the setting parameters of the apparatus configuration are sorted according to whether they are or are not affected by the version conflict. As a result, the unaffected setting parameters can be used despite the occurrence of the conflict, so that the operation can thus be continued. Reliability and safety are substantially increased, since the respiration operation is guaranteed independently from a completed or neglected software update.

A further advantage is that the setting parameters are retained and remain usable despite a version conflict. As a result, a frequently time-consuming re-entry of the setting parameters is not required. Furthermore, it is particularly advantageous that even an apparatus software program or apparatus configuration with an invalid version can be used for the operation of the respiration apparatus. This is particularly helpful if, for example, the facility or time is not immediately available to carry out an update.

The validity of a version is determined in particular on the basis of at least a current status. In particular, a newer version is valid. An older version is, in particular, invalid.

In particular, a newer version is valid rather than an older version. However, it is also possible and preferable for the validity of a version to be determined on the basis of at least one allocated priority. In particular, a version with a higher priority is valid rather than a version with a lower priority.

In a comparison with a different version, the priority of a version is, for example, more heavily weighted than a current status. Thus, for example, an older version with a higher priority can be acknowledged as valid rather than a newer version with a lower priority. The version and, in particular, the current status and/or priority are preferably stored and readable as at least one program element in the apparatus software and/or the apparatus configuration. The versions are preferably checked before and/or during an installation.

The apparatus configuration and the apparatus software are preferably stored in at least one storage device. The apparatus configuration and the apparatus software can also be stored in each case in a separate storage device, e.g. a memory card and a permanently installed memory.

Within the meaning of this invention, the setting parameters are in particular those values which define the setting of specific apparatus parameters. Apparatus parameters are, for example, a pressure, flow, rotational speed, periodicity or the like. The setting parameter specifies, in particular, a value or value range for an apparatus parameter of this type, e.g. a value for a pressure. The setting parameter may also be designed as at least one function and/or at least one algorithm. An algorithm as a setting parameter describes, for example, the increase or decrease in a pressure over time to specific values. Particularly preferably, the setting parameters specify values with which the respiration parameters to be set for the respiration are set to specific values and or progressions.

The setting parameters of the second group are, in particular, characterized in that they are retrieved in the case of an envisaged operation of the apparatus software and are not stored in the apparatus configuration. The setting parameters of the second group can also be characterized in that they are not needed in an operation and are not retrieved by the apparatus software. The setting parameters that are not required are preferably not retained. The setting parameters of the second group are, in particular, incompatible if an impermissible combination of apparatus software and apparatus configuration occurs.

In one particularly preferred refinement, the setting parameters of the second groups are sorted into at least a first class and at least a second class. The first class comprises setting parameters that are uncritical for an envisaged operation of the respiration apparatus. The second class comprises, in particular, setting parameters that are critical for an envisaged operation.

Setting parameters are defined as uncritical particularly if at least one alternative allocation is possible despite the version conflict. For example, uncritical setting parameters can be recalculated, skipped, deleted and/or replaced by at least one other setting parameter. If no alternative allocation is possible for an uncritical setting parameter, an at least partial operation may nevertheless be possible.

Critical setting parameters are characterized, in particular, in that they are necessary for at least one function of the respiration apparatus and this function cannot be provided correctly due to the version conflict. In particular, a critical setting parameter is incompatible in relation to the apparatus software.

A critical setting parameter must, in particular, be reconfigured in order to be compatible with the apparatus software. For example, a setting parameter may be critical because it specifies a value that is not settable by means of the apparatus software and/or the respiration apparatus that is used. It is also possible that its value is settable, but the apparatus software contains a component which prohibits or does not permit the setting of such a value.

Such a division of the setting parameters concerned into a critical and uncritical class enables a prompt evaluation of the version conflict and therefore simplifies the taking into account of the necessary steps for at least partially eliminating the version conflict.

At least one setting parameter of the first class is preferably recalculated. In particular, at least one rule stored in the apparatus software is taken into account for the calculation. For example, the apparatus software may comprise at least one algorithm that is used to recalculate a setting parameter. In particular, as a consequence of the recalculation, the setting parameter can be accepted or used despite the version conflict, in particular for the apparatus configuration.

A recalculation of this type has the advantage that even newer apparatuses and apparatuses with newer apparatus software can be set and operated by means of an older apparatus configuration, although the apparatus configuration does not initially provide all necessary setting parameters for such a combination of versions. The recalculation rule may also originate from a source other than the apparatus software, for example from an external software program or the apparatus configuration itself.

It is possible for the recalculation rule to provide at least a taking into account of at least one setting parameter associated with the first group. A taking into account of a setting parameter associated with the second group can also be provided. In particular, at least one interdependency of at least two setting parameters is established on the basis of the taking into account.

The recalculation is carried out, in particular, on the basis of the interdependent setting parameters. Setting parameters that have already been accepted and/or retained and/or reconfigured are preferably taken into account. Critical setting parameters are, in particular, not taken into account for the recalculation of other critical setting parameters. The adjustment of critical setting parameters is considerably simplified through the inclusion of the interdependencies.

In one advantageous embodiment, at least one setting parameter of the first class is set using at least one user input. For example, the value for the setting parameter can be directly entered manually. Different values can also be proposed to the user, from which he selects a suitable value. A transfer of setting parameters from a different apparatus configuration and/or from an external computer is also possible. A user input of this type enables a fast and uncomplicated replacement of setting parameters.

At least one setting parameter of the first class is particularly preferably replaced by at least one default setting. The default setting is preferably stored in at least one storage device. An acceptance of large parts of and/or a complete default setting is also possible. The default setting can also replace a plurality and/or all setting parameters of the classes.

In particular cases, critical setting parameters of the second class can also be replaced by at least one default setting. It can be provided that the default setting offers an only partially adequate replacement for the critical setting parameter. In the case of an inadequate assignment of the critical setting parameters, an operation in a safe mode and/or an emergency mode, for example, can be provided. Here, at least one indication is preferably output to the user. A replacement of setting parameters with corresponding default settings offers a reliable facility for quickly and simply correcting incompatibilities occurring in a version conflict.

It is possible and preferred that, if at least one setting parameter of the second class is present, an indication of the version conflict is output to the user. The indication may, for example, comprise a prompt to update the apparatus software and/or the apparatus configuration. A valid combination can be proposed. It is also possible for a reference source to be specified and/or a connection to be set up to a reference source, e.g. via the Internet. It is possible for operation to be stopped or carried out in a restricted manner until the update.

It is also possible and preferred that, if at least one setting parameter of the second class is present, at least one user input is required. In particular, a previous and in particular valid version of the apparatus software is restored after the user input. It is also possible for a previous and valid version of the apparatus configuration and/or of an external software program to be restored. The previous version is preferably stored in at least one storage device.

For example, at least one backup is created before the performance of a software update and/or an update of the apparatus configuration. An updating process, for example, is interrupted by the user input while said process may already have started. The detection and checking of the versions are particularly preferably carried out before an update and, in particular before an installation of a new software program or configuration.

If at least one setting parameter of the second class is present, at least one user input may also be required which releases an operation with an invalid version of the apparatus software and apparatus configuration. In particular, following the user input, the operation is continued with the invalid version in an at least partially restricted mode. For example, only a part of the apparatus function may be usable and/or the operation is continued with setting parameters which correspond only partially to those required by the user.

It is possible for at least one setting parameter to be stored in a storage device for a restricted mode of this type, by means of which critical setting parameters and/or missing setting parameters are supplemented or reconfigured. A design of this type then offers a use of the apparatus even if version conflicts occur due to missing and/or inadequate updates.

The method according to the invention serves to operate at least one respiration system. The respiration system comprises at least one respiration apparatus and at least one computer software for an external computer to operate the respiration apparatus via at least one interface. The respiration apparatus has at least one processor device to control a plurality of apparatus functions. The processor device comprises at least one apparatus software program and at least one apparatus configuration with setting parameters. A validity of the computer software, a validity of the apparatus software and a validity of the apparatus configuration are in each case characterized by at least one version. The versions are compared at least partially with one another in order to detect a version conflict. At least one program component is provided by the apparatus software for the computer software if an invalid version of the computer software and a valid version of the apparatus software are detected. The program component comprises at least one limit value. Furthermore, the program component comprises at least one plausibility rule. At least one setting parameter can be set in the apparatus configuration from the computer software using the plausibility rule and the limit value.

The respiration system according to the invention offers the advantage that the apparatus software provides the computer software with at least one program component with a limit value and a plausibility rule. As a result, the computer software can control the respiration apparatus even if a version conflict results in incompatibilities.

Furthermore, the method for operating the respiration system is advantageously supplemented with the method for operating the respiration apparatus. The operation of the respiration apparatus can be maintained and respiration can be guaranteed with a combination of this type, totally independently from versions of the computer software, the apparatus software and the apparatus configuration.

For example, even a computer with an out-of-date and invalid computer software program can therefore be used to control or read a respiration apparatus with a new and valid apparatus software program or apparatus configuration.

Even setting parameters for which the computer software version is not designed can be used from the invalid computer software by means of the program component. A safe and reliable operation of the respiration system, independently from software updates, is thereby guaranteed.

In particular, at least one limit value is stored for at least one setting parameter. In particular, the setting parameters affected by the version conflict and, for example, uncritical and/or critical setting parameters can be adjusted using the limit value. It is possible that an invalid version of the apparatus configuration is also present.

An adaptation of the apparatus configuration can also be provided here, for example as previously described for the method for operating the respiration apparatus. The apparatus configuration may also be valid. It may be provided that an at least partially restricted operation of the computer software is possible despite the program component that is provided. For example, only a part of the functions of the respiration apparatus can be accessed from the computer software. It is also possible that only a part of the apparatus configuration can be influenced from the computer software.

In a preferred refinement, at least one interdependency between at least two setting parameters is defined by the program component. An interdependency between three or four or a plurality of setting parameters is also possible. This substantially improves the accuracy of a reconfiguration of setting parameters.

In a particularly preferred refinement, at least one program code is provided by the program component. The program code is preferably stored in at least one program library jointly used by the apparatus software and the computer software. This has the advantage that both the apparatus software and the computer software simultaneously access and/or can influence the program component. A further advantage is that a change in the program component by the apparatus software also impacts immediately on the computer software and vice versa.

The program code is particularly preferably provided by at least one executable file. In particular, the program code is provided by a DLL file and/or a comparable suitable file. A design of this type is particularly well suited for providing the program components for the invalid computer software which said software requires for fault-free communication with the apparatus software.

The computer software is preferably designed as at least partially backward-compatible. In particular, the computer software is suitable and designed to be operated by at least one version of an apparatus software program detected as invalid and/or to operate such a software program. In particular, the computer software is designed so that it is operable in the proposed manner with at least one invalid and, in particular, older version of an apparatus software program and/or an apparatus configuration. A design of this type has the advantage that even older respiration apparatuses can be set and/or read from newer computers.

The methods can also be designed so that a parallel setting of a multiplicity of apparatus configurations can be undertaken by means of at least one master program. The master program is, in particular, executable with valid versions only. In particular, the apparatus configurations relate to different respiration apparatuses. A master program of this type has the advantage that a simple and uncomplicated setting of the apparatus configurations can thereby be effected for a plurality of respiration apparatuses. Since a plurality of respiration apparatuses are normally involved here and settings that are decisive for the respiration are also frequently defined, the program execution linked to valid versions provides a high degree of safety.

The methods can also provide at least one auxiliary program which serves, in particular, for program-based setting of at least one apparatus configuration. In particular, at least one rule for a setting of at least one setting parameter is defined by the auxiliary program.

The auxiliary program may, for example, contain a rule specifying which setting parameters are accepted and/or reset and/or deleted. The rule may also contain limit values for the setting of setting parameters. It is possible for the auxiliary program or its executability to be linked to a specific combination of versions. An auxiliary program of this type has the advantage that the setting parameters can be automatically adjusted in the apparatus configurations following an update or if version conflicts occur.

The respiration apparatus according to the invention comprises at least one processor device to control a plurality of apparatus functions. The processor device has at least one apparatus software program and at least one apparatus configuration with setting parameters. A validity of the apparatus software and a validity of the apparatus configuration are characterized in each case by at least one version. The processor device is suitable and designed to compare the versions at least partially with one another in order to detect a version conflict between the apparatus software and the apparatus configuration. The processor device is suitable and designed to register at least one invalid version of the apparatus configuration and at least one valid version of the apparatus software. The processor device is furthermore suitable and designed to read the setting parameters of the apparatus configuration and sort them into at least a first group with setting parameters unaffected by the version conflict and at least a second group with setting parameters affected by the version conflict. The processor device is suitable and designed to retain the setting parameters of the first group.

The respiration apparatus is particularly preferably designed in such a way that it is operable with the method according to the invention and its refinements. As a result, the method can be particularly effectively implemented and its advantages exploited.

The respiration system according to the invention comprises at least one respiration apparatus and at least one computer software program for an external computer to operate the respiration apparatus via at least one interface. The respiration apparatus comprises at least one processor device to control a plurality of apparatus functions. The processor device has at least one apparatus software program and at least one apparatus configuration with setting parameters. A validity of the computer software, a validity of the apparatus software and a validity of the apparatus configuration are characterized in each case by at least one version. The processor device is suitable and designed to compare the versions at least partially with one another in order to detect a version conflict. The processor device is suitable and designed to register a valid version of the apparatus software and an invalid version of the computer software and to provide at least one program component stored in the apparatus software for the computer software. The program component comprises at least one limit value and at least one plausibility rule for the computer software. At least one setting parameter is settable in the apparatus configuration from the computer software using the program component.

The respiration system is preferably designed so that it is operable with the method according to the invention and its refinements. The advantages of the method can thereby be particularly effectively exploited. The respiration system preferably also comprises a respiration apparatus which is designed in the same way as the respiration apparatus described above. A combination of this type provides a particularly reliable respiration operation which can be guaranteed independently from software updates.

BRIEF DESCRIPTION OF THE DRAWING

Further advantages and features of the present invention can be found in the description of the example embodiment which is explained below with reference to the attached FIGURE.

FIG. 1 shows a respiration apparatus 1 according to the invention.

DETAILED DESCRIPTION OF EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawing making apparent to those of skill in the art how the several forms of the present invention may be embodied in practice.

FIG. 1 shows a respiration system 100 with a respiration apparatus 1 and a predominantly schematically represented computer 10. The respiration apparatus 1 is preferably a home respiration apparatus 11. The respiration system 100 and the respiration apparatus 1 are provided and designed here to carry out the method according to the invention.

The respiration apparatus 1 comprises a respiration device 2 with a ventilator device 3 to generate an air flow for the respiration surrounded by a housing 101. A monitoring device 5 with a storage device 15, a controller 25 and a sensor device 35 are provided to control the respiration device 2.

The respiration apparatus 1 is operated and set via an operating device 7 with a display unit 17 and an interface for the data exchange 27. A humidifying device 6 is provided to increase the humidity content of the respiratory air.

The respiration apparatus 1 has a respiration interface 4 to feed the air flow to a user for respiration. The respiration interface is preferably designed as a patient interface that is conventional in respiration apparatuses and, for example, as a full face mask or as a nasal pillow or as a tube or as a larynx mask. The respiration interface 4 shown here is a respiratory mask 14 designed as a nasal mask. A hood 24 is provided to attach the respiratory mask 14.

A connection tube 54 which is connected by means of a coupling device 64 to the respiration device 2 is provided in order to connect the respiration interface 4 to the respiration device 2. The connection tube 54 is connected via a coupling element 34 to the respiration interface 4. An exhalation element 44 comprising a valve or designed as such is disposed between the connection tube 54 and the coupling element 12. The exhalation element 44 is provided, in particular, to prevent respiration back into the respiration apparatus 1 during the exhalation of the user.

The monitoring device 5 is actively connected to the sensor device 35 which has one or more sensors to measure variables that are characteristic of the respiration parameters. For example, the sensor device 35 has a pressure sensor (not shown here) which measures the pressure ratios in the area of the respiration interface. To do this, the pressure sensor has a flow connection via a pressure-measuring tube 350 to the respiration interface 4.

The pressure-measuring tube 350 extends from the respiration interface 4 along the connection tube 54 to an input nozzle 351 on the housing 101. The pressure-measuring tube 350 has a flow connection via the input nozzle 351 to the pressure sensor of the sensor device 35.

The flow is measured via a restrictor which is arranged in the main channel of the flow connection between the ventilator device and the respiration interface 4. An arrangement in a secondary channel is also possible. In order to monitor further respiratory parameters, the sensor device 35 can also be equipped with sensors to measure the respiratory excursion, to measure an oxygen saturation of the blood and/or to measure an EEG, EMG, EOG or ECG activity.

Furthermore, the monitoring device 5 has a controller 25 to control the ventilator device 3. The controller 25 provides a necessary minimum pressure and compensates for pressure fluctuations caused by the respiratory activity of the user. For example, the controller 25 also measures the prevailing pressure in the respiratory mask 14 and readjusts the output of the ventilator device 3 accordingly until a required respiratory pressure is applied.

The respiration apparatus 1 shown here may be designed as a fixed-level apparatus or as an automatic-level apparatus. In particular, an adjustment is carried out by the monitoring device 5 in line with reference values that have previously been calculated and defined individually on the basis of the characteristic breathing of a user.

It is also possible for the respiration device 2 to be adapted dynamically and in particular according to the respiratory phase of the user. For example, a respiratory phase change can be detected using the monitoring device 5, so that a higher or lower pressure can be provided according to the respiratory phase. For example, the respiration apparatus 1 can be designed as a CPAP or APAP apparatus. The respiration apparatus 1 can also be designed as a bi-level apparatus. For example, the respiration apparatus 1 responds to specific respiratory events, such as e.g. snoring, respiratory flattening and/or obstructive pressure peaks with corresponding settings of the respiratory parameters.

The respiration apparatus 1 has a processor device 8 here in order to operate the apparatus components and control the apparatus functions that are provided, in particular, by these apparatus components. The apparatus components are e.g. the respiration device 2, the ventilator device 3, the monitoring device 5, the humidifying device 6, the operating device 7, the storage device 15, the display unit 17, the controller 25, the interface 27 and the sensor device 35, and also further apparatus components not shown here.

The processor device 8 is designed here as a microcomputer and comprises an apparatus software program as well as an operating system. With the processor device 8, data can be exchanged with the external computer 10. The processor device 8 and the computer 10 are interconnected via the interface 27 of the respiration apparatus 1. The interface 27 may also be designed for wireless communication.

A multiplicity of apparatus functions can be operated and set from the external computer. To do this, the computer 10 has a computer software program with a user interface by means of which settings can be performed simply and clearly. Data, such as e.g. respiration statistics, error messages, current settings or other data stored in the storage device 25 or the processing device 8 can also be retrieved from the respiration apparatus 1 by means of the computer software. The computer software also comprises e.g. a program for evaluating the respiration statistics.

A apparatus configuration is stored in order to adapt the apparatus software to the respiration apparatus 1. The apparatus configuration may comprise, for example, one or more files and may be stored in the storage device 15 or on a memory card which is inserted into the apparatus 1. The apparatus configuration comprises a multiplicity of setting parameters according to which the individual apparatus functions and e.g. the respiration device 2 are configured and operated.

The versions of the computer software, the apparatus software and the apparatus configuration, also referred to below as operating programs, are compared with one another in order to detect version conflicts. This can be done, for example, when the computer 100 is started up or when the respiration apparatus 1 is switched on, or after or before an update.

In order to maintain a compatibility of the operating programs with one another and thus guarantee a reliable operation of the respiration apparatus 1 despite different versions, a series of measures are provided according to the invention, some of which are presented here by way of example.

For example, the apparatus software has been updated and used in an apparatus 1 with an old and therefore invalid apparatus configuration. For example, a new apparatus software program can also be used for an apparatus 1 that is not yet supported. In such cases, the apparatus 1 must then be set with an apparatus configuration originating from an older apparatus or software version.

To maintain the compatibility of the operating programs, the setting parameters stored in the apparatus configuration are read out and sorted according to whether they are or are not affected by the version conflict. The setting parameters unaffected by the version conflict are accepted unchanged.

The remaining setting parameters are then divided up according to whether they can uncritically or critically affect the operation of the respiration apparatus 1. Newly added, uncritical setting parameters are then appropriately configured in such a way that either default settings are adopted or logically appropriate parameter values are determined from the other setting parameters. As a consequence of critical setting parameters becoming incompatible or being newly added, either the user must dissolve the dependency or the overall configuration is not accepted.

A different measure can be undertaken, for example, if an old and therefore invalid configuration and a new, updated apparatus software program are present. In the case of an apparatus software update, a check is carried out before the update to determine whether the settings specified by the apparatus configuration can be accepted in a suitable manner with the new version. If this cannot be done in the required manner, a corresponding notification to the user is generated. If no suitable acceptance is possible, the user has the facility to interrupt the update process. Alternatively, he can carry out the update, wherein the apparatus 1 then uses the default settings. If an acceptance is possible but requires decisions on the part of the user for individual configuration settings, these settings can similarly be retrieved.

For specific setting parameters or subsets of setting parameters, the apparatus software can define requirements for the transfer from an invalid into a valid, new configuration. These requirements can be provided for specific combinations of versions of the operating programs. The acceptance of a new configuration is thereby considerably speeded up and simplified. For example, a requirement of this type may indicate which setting parameters are accepted and which are not accepted. Respiration parameters such as reference pressure, for example, can be accepted, but not comfort parameters, such as display brightness, or vice versa.

For example, an invalid apparatus configuration may have a setting parameter with a value of 27 hPa. In a new, valid apparatus configuration, the setting parameter may then comprise e.g. a value range from 4 to 25 hPa. The setting parameter is then accepted into the valid configuration, for example, using an automatic reset to a value of 25 hPa.

The measures presented above enable a transfer from an apparatus configuration that was valid in a first apparatus software version into a new apparatus configuration which is then valid in a second, more up-to-date apparatus software version. The transfer is effected via at least one set of rules which takes account of interdependencies and priorities and also limit values and plausibility rules or other suitable adaptation instruments.

Updates for the apparatus software can thereby be loaded without the previous settings becoming meaningless or invalid or even without the apparatus 1 switching to an undefined state or having to be completely reconfigured. By means of such measures, it is furthermore ensured that apparatus configurations can be used on different respiration apparatuses 1 if these configurations were created with an old software version and were dispatched, for example, via a data medium.

The method also enables an operation of newer respiration apparatuses 1 with computers 100 which have older and therefore invalid versions of the computer software. If a valid apparatus software program and an invalid computer software program are present, the apparatus software provides, for example, a program component with which the computer software can be extended or updated, as a result of which the support of the respiration apparatus from the older computer software is enabled. The program component may be provided, for example, via a memory card, via a USB mass storage device or via LAN or WLAN.

The program component is, for example, a file that defines parameter limits and plausibility rules. The file may additionally also define parameter interdependencies. The file is then read and used accordingly by the computer software. The program component may also be designed e.g. as a functional software component, such as e.g. a DLL file. The computer software is enabled by the DLL file provided by the apparatus software to interact with the respiration apparatus 1.

An interaction between the computer 100 and the respiration apparatus 1 is thus enabled by the program component despite invalid versions. As a result, the computer software can provide functions not previously possible or accessible and, in particular, can read and control the respiration apparatus 1. This is particularly advantageous if a new apparatus type is placed on the market, since the external computers 100 would not be able to support the new apparatus 1 without the provision of the program component by the apparatus software.

A reliable operation of the respiration system 100 is also achieved by keeping the computer software backward-compatible in the development process. As a result, a new computer software program can also support older devices 1 with invalid apparatus software. When a connection is set up between a computer 100 and a respiration apparatus 1, e.g. the type and apparatus software version are queried and the configuration is carried out according to the version. If it is detected that a critical update for the apparatus software is defined as a mandatory requirement, this is requested e.g. via a notification to the user.

In the event of a discrepancy between the versions of the operating programs to such an extent reliable operation is no longer guaranteed, an update request can be provided. It can be defined here, for example for the respectively newer component, the computer software and/or the apparatus software, that the latter blocks the interaction with older versions of the three operating programs and requests an update of the respectively older and invalid operating programs.

A master program is provided in the case where a multiplicity of devices 1 are to be configured in an identical manner. The master program is stored, for example, on a memory card. An apparatus configuration or e.g. a basic configuration can thus be quickly and simply stored on a multiplicity of devices 1. Since it is particularly important in such a case that no version conflicts occur, the execution of the master program can be blocked if invalid versions are present.

The method for the respiration system and the method for the respiration apparatus can also be advantageously operated in parallel, e.g. within a respiration system. The respiration apparatus is e.g. a bi-level apparatus which is initially operated in an S/T mode with IPAP and EPAP and has set a multiplicity of further parameters. In the event of an apparatus update, EPAP and the further parameters can be accepted unchanged. A further apparatus alarm, for example, is added. The default setting ("inactive") can be accepted into the new apparatus configuration for this alarm.

Furthermore, a target volume function, for example, is added. This means that IPAPmax and IPAPmin rather than IPAP must be set in future in S/T mode, and additionally the target volume VTarget. There is no generally valid default setting for IPAPmax, IPAPmin and VTarget, and these must be selected individually for the patient requiring respiration. The apparatus software detects this conflict during the update by means of the adaptation of the apparatus configuration or by means of the program component. It asks the user, e.g. the doctor or technician, for the values that are to be used for IPAPmax, IPAPmin and VTarget for the patient currently requiring respiration. Via the program component, it knows the applicable value range of the new parameters and the IPAP>=IPAPmin interrelationship. The selection facility of the user is thereby appropriately restricted. If the setting is effected during the update or at a later time via a computer software program, the latter learns the value limits and interrelationship of the new parameters via the program component. Although the target volume function was not yet present at the time when the computer software was created, the apparatus can nevertheless be set correctly via the computer software.

The methods and devices presented here have the advantage that as many combinations as possible of different versions of computer software and/or apparatus software and/or apparatus configurations are usable with one another. As a result, as many user settings and respiration settings as possible can be accepted following an update. In addition, it is thereby guaranteed that the resulting respiration function is safe and defined.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

To sum up, the present invention provides:
1. A method for operating at least one respiration apparatus with at least one processor device to control a plurality of apparatus functions comprising at least one apparatus software program and at least one apparatus configuration with setting parameters, wherein a validity of the apparatus software and a validity of the apparatus configuration are characterized in each case by at least one version and wherein the versions are compared with one another in order to detect a version conflict between the apparatus software and the apparatus configuration, and wherein, if an invalid version of the apparatus configuration and a valid version of the apparatus software are present, the setting parameters of the apparatus configuration are read and sorted into at least a first group with setting parameters that are unaffected by the version conflict and at least a second group with setting parameters that are affected by the version conflict and that the setting parameters of the first group are retained.
2. The method according to item 1, wherein the setting parameters of the second group are sorted into at least a first class with setting parameters that are uncritical for an envisaged operation of the respiration apparatus and at least a second class with setting parameters that are critical for an envisaged operation of the respiration apparatus.
3. The method according to item 1 or item 2, wherein at least one setting parameter of the first class is recalculated on the basis of at least one rule stored in the apparatus software.
4. The method according to item 3, wherein the calculation rule provides a taking into account of at least one other setting parameter of the first group and/or the second group.
5. The method according to any one of items 2 to 4, wherein at least one setting parameter of the first class is set using at least one user input.
6. The method according to any one of claims 2 to 5, wherein at least one setting parameter of the first class is replaced with at least one default setting stored in a storage device.
7. The method according to any one of items 2 to 6, wherein, if at least one setting parameter of the second class is present, at least one indication of the version conflict is output to the user.
8. The method according to any one of items 2 to 7, wherein, if at least one setting parameter of the second class is present, a preceding and valid version of the apparatus software is restored following a request for at least one user input.
9. The method according to any one of items 2 to 8, wherein, if at least one setting parameter of the second class is present, at least one user input is requested for an operation with the invalid version of the apparatus software and apparatus configuration and, following the user input, the operation is continued with the invalid version in an at least partially restricted mode.
10. A method for operating at least one respiration system with at least one respiration apparatus and with at least one computer software program for an external computer for operating the respiration apparatus via at least one interface, wherein the respiration apparatus comprises at least one processor device to control a plurality of apparatus functions, the processor device comprising at least one apparatus software program and at least one apparatus configuration with setting parameters, wherein a validity of the computer software and a validity of the apparatus software and a validity of the apparatus configuration are characterized in each case by at least one version and wherein the versions are compared at least partially with one another in order to detect a version conflict, and wherein, if a valid version of the apparatus software and an invalid version of the computer software are present, at least one program component for the computer software is provided by the apparatus software and the program component defines at least one limit value and at least one plausibility rule for the computer software, by means of which at least one setting parameter can be set in the apparatus configuration from the computer software.
11. The method according to item 10, wherein at least one interdependency between at least two setting parameters is defined by the program component.
12. The method according to item 10 or item 11, wherein at least one program code is provided by the program component in at least one program library jointly used by the apparatus software and the computer software.
13. The method according to item 12, wherein the program code is provided by at least one executable file and, in particular, at least one DLL file.
14. The method according to any one of items 10 to 13, wherein the computer software is designed as at least partially backward-compatible, so that an operation is possible with at least one version of an apparatus software program recognized as invalid.
15. The method according to any one of items 1 to 14, wherein a parallel setting of a multiplicity of apparatus configurations is undertaken by means of at least one master program and wherein the master program is executable with valid versions only.
16. The method according to any one of items 1 to 15, wherein at least one auxiliary program is used to set the apparatus configuration, by means of which at least one rule is defined for setting at least one setting parameter.
17. A respiration apparatus with at least one processor device to control a plurality of apparatus functions comprising at least one apparatus software program and at least one apparatus configuration with setting parameters, wherein a validity of the apparatus software and a validity of the apparatus configuration are characterized in each case by at least one version and wherein the processor device is suitable and designed to compare the versions at least partially with one another in order to detect a version conflict between the apparatus software and the apparatus configuration, and wherein the processor device is suitable and designed to register at least one invalid version of the apparatus configuration and at least one valid version of the apparatus software and to read the setting parameters of the apparatus configuration and sort them into at least a first group with setting parameters unaffected by the version conflict and at least a second group with setting parameters affected by the version conflict and to retain the setting parameters of the first group.
18. A respiration system with at least one respiration apparatus and with at least one computer software program for an external computer to operate the respiration apparatus via at least one interface, wherein the respiration apparatus comprises at least one processor device to control a plurality of apparatus functions, the processor device having at least one apparatus software program and at least one apparatus configuration with setting parameters, wherein a validity of the computer software, a validity of the apparatus software and a validity of the apparatus configuration are characterized in each case by at least one version and wherein the processor device is suitable and designed to compare the versions at least partially with one another in order to detect a version conflict, and wherein the processor device is suitable and designed to register a valid version of the apparatus software and an invalid version of the computer software and to provide at least one program component stored in the apparatus software for the computer software and the program component comprises at least one limit value and at least one plausibility rule for the computer software, by means of which at least one setting parameter is settable in the apparatus configuration from the computer software.

LIST OF REFERENCE NUMBERS

1 Respiration apparatus
2 Respiration device
3 Ventilator device
4 Respiration interface
5 Monitoring device
6 Humidifying device
7 Operating device
8 Processor device
11 Home respiration apparatus
10 Computer
14 Respiratory mask
15 Storage device
17 Display unit
24 Hood
25 Controller
27 Interface
34 Coupling element
35 Sensor device
44 Exhalation element
54 Connection tube
64 Coupling device
100 Respiration system
101 Housing
350 Pressure-measuring tube
351 Input nozzle

What is claimed is:

1. A method for operating at least one respiration apparatus with at least one processor device to control a plurality of apparatus functions comprising at least one apparatus software program and at least one apparatus configuration with setting parameters, wherein a validity of the apparatus software and a validity of the apparatus configuration are characterized in each case by at least one version and wherein the versions are compared with one another in order to detect a version conflict between the apparatus software and the apparatus configuration, wherein, if an invalid version of the apparatus configuration and a valid version of the apparatus software are present, the setting parameters of the apparatus configuration are read and sorted into at least a first group with setting parameters that are unaffected by the version conflict and at least a second group with setting parameters that are affected by the version conflict, and wherein the setting parameters of the first group are retained and the setting parameters of the second group are sorted into at least a first class with setting parameters that are uncritical for an envisaged operation of the respiration apparatus and at least a second class with setting parameters that are critical for an envisaged operation of the respiration apparatus.

2. The method of claim 1, wherein at least one setting parameter of the first class is recalculated on the basis of at least one calculation rule stored in the apparatus software.

3. The method of claim 2, wherein the calculation rule provides a taking into account of at least one other setting parameter of the first group and/or the second group.

4. The method of claim 1, wherein at least one setting parameter of the first class is set using at least one user input.

5. The method of claim 1, wherein at least one setting parameter of the first class is replaced with at least one default setting stored in a storage device.

6. The method of claim 1, wherein, if at least one setting parameter of the second class is present, at least one indication of the version conflict is output to the user.

7. The method of claim 1, wherein, if at least one setting parameter of the second class is present, a preceding and valid version of the apparatus software is restored following a request for at least one user input.

8. The method of claim 1, wherein, if at least one setting parameter of the second class is present, at least one user input is requested for an operation with the invalid version of the apparatus software and apparatus configuration and, following the user input, the operation is continued with the invalid version in an at least partially restricted mode.

9. The method of claim 1 for operating at least one respiration system with at least one respiration apparatus and with at least one computer software program for an external computer for operating the respiration apparatus via at least one interface, wherein the respiration apparatus comprises at least one processor device to control a plurality of apparatus functions and wherein the processor device comprises at least one apparatus software program and at least one apparatus configuration with setting parameters, wherein a validity of the computer software and a validity of the apparatus software and a validity of the apparatus configuration are characterized in each case by at least one version and wherein the versions are compared at least partially with one another in order to detect a version conflict, and wherein, if a valid version of the apparatus software and an invalid version of the computer software are present, at least one program component for the computer software is provided by the apparatus software, the program component defining at least one limit value and at least one plausibility rule for the computer software, by which at least one setting parameter can be set in the apparatus configuration from the computer software.

10. The method of claim 9, wherein at least one interdependency between at least two setting parameters is defined by the program component.

11. The method of claim 9, wherein at least one program code is provided by the program component in at least one program library jointly used by the apparatus software and the computer software.

12. The method of claim 11, wherein the program code is provided by at least one executable file.

13. The method of claim 12, wherein the program code is provided by at least one DLL file.

14. The method of claim 9, wherein the computer software is designed as at least partially backward-compatible, so that an operation is possible with at least one version of an apparatus software program recognized as invalid.

15. The method of claim 9, wherein a parallel setting of a multiplicity of apparatus configurations is undertaken by at least one master program and wherein the master program is executable with valid versions only.

16. The method of claim 9, wherein at least one auxiliary program is used to set the apparatus configuration, by which at least one rule is defined for setting at least one setting parameter.

17. A respiration apparatus with at least one processor device to control a plurality of apparatus functions comprising at least one apparatus software program and at least one apparatus configuration with setting parameters, wherein a validity of the apparatus software and a validity of the apparatus configuration are characterized in each case by at least one version and wherein the processor device is suitable and designed to compare the versions at least partially with one another in order to detect a version conflict between the apparatus software and the apparatus configuration, and wherein the processor device is suitable and designed to register at least one invalid version of the apparatus configuration and at least one valid version of the apparatus software and to read the setting parameters of the apparatus configuration and sort them into at least a first group with setting parameters unaffected by the version conflict and at least a second group with setting parameters affected by the version conflict and to retain the setting parameters of the first group and to sort the setting parameters of the second group into at least a first class with setting parameters that are uncritical for an envisaged operation of the respiration apparatus and at least a second class with setting parameters that are critical for an envisaged operation of the respiration apparatus.

18. A respiration system with at least one respiration apparatus according to claim 17 and with at least one computer software program for an external computer to operate the respiration apparatus via at least one interface, wherein the respiration apparatus comprises at least one processor device to control a plurality of apparatus functions and wherein the processor device has at least one apparatus software program and at least one apparatus configuration with setting parameters, wherein a validity of the computer software, a validity of the apparatus software and a validity of the apparatus configuration are characterized in each case by at least one version and wherein the processor device is suitable and designed to compare the versions at least partially with one another in order to detect a version conflict, is suitable and designed to register a valid version of the apparatus software and an invalid version of the computer software and to provide at least one program component stored in the apparatus software for the computer software, the program component comprising at least one limit value and at least one plausibility rule for the computer software, by which at least one setting parameter is settable in the apparatus configuration from the computer software.

* * * * *